US012751830B2

(12) United States Patent
Lindner

(10) Patent No.: US 12,751,830 B2
(45) Date of Patent: Oct. 6, 2026

(54) KNEE-JOINT ENDOPROSTHESIS

(71) Applicant: Aesculap AG, Tuttlingen (DE)

(72) Inventor: Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 372 days.

(21) Appl. No.: 18/560,815

(22) PCT Filed: May 18, 2022

(86) PCT No.: PCT/EP2022/063392
§ 371 (c)(1),
(2) Date: Nov. 14, 2023

(87) PCT Pub. No.: WO2022/243353
PCT Pub. Date: Nov. 24, 2022

(65) Prior Publication Data

US 2024/0245520 A1 Jul. 25, 2024

(30) Foreign Application Priority Data

May 18, 2021 (DE) ..................... 10 2021 205 048.4

(51) Int. Cl.
*A61F 2/38* (2006.01)
*A61F 2/30* (2006.01)

(52) U.S. Cl.
CPC .... *A61F 2/389* (2013.01); *A61F 2002/30014* (2013.01); *A61F 2002/3008* (2013.01);
(Continued)

(58) Field of Classification Search
CPC .... A61F 2/30; A61F 2/38; A61F 2/389; A61F 2/3868; A61F 2/3859; A61F 2/3886
See application file for complete search history.

(56) References Cited

U.S. PATENT DOCUMENTS 5,645,604 A 7/1997 Schneider et al.
6,126,692 A 10/2000 Robie et al.
(Continued)

FOREIGN PATENT DOCUMENTS

DE 202008004709 U1 7/2008

OTHER PUBLICATIONS

Search Report received in International Application No. PCT/EP2022/063392 dated Aug. 23, 2022, with translation, 5 pages.

*Primary Examiner* — Christopher J Beccia
(74) *Attorney, Agent, or Firm* — Christopher A. Rothe; CM Law

(57) ABSTRACT

A knee-joint endoprosthesis includes a tibia component for proximal fixation to a tibia. The tibia component has a form-fitting section arranged on an upper face. The endoprosthesis also has a meniscus component configured to articulate with a femoral joint component. The meniscus component has a complementary form-fitting section arranged on a lower face. The tibia component and the meniscus component are joined together by a form-fitting connection formed between the form-fitting section and the complementary form-fitting section. At least one reinforcement element is inserted into the meniscus component and is configured to mechanically reinforce the form-fitting joint connection. The reinforcing element is arranged in the region of the complementary form-fitting section.

13 Claims, 6 Drawing Sheets

(52) U.S. Cl.
CPC ............... *A61F 2002/30492* (2013.01); *A61F 2002/305* (2013.01)

(56) References Cited

U.S. PATENT DOCUMENTS

| | | | | |
|---|---|---|---|---|
| 9,005,300 | B2 | 4/2015 | Collazo | |
| 2014/0067076 | A1 * | 3/2014 | Collazo | A61F 2/389 623/20.32 |
| 2014/0256229 | A1 * | 9/2014 | Zhang | A61F 2/30767 451/39 |

* cited by examiner

KNEE-JOINT ENDOPROSTHESIS

CROSS-REFERENCE TO RELATED APPLICATION(S)

This application is the United States national stage entry of International Application No. PCT/EP2022/063392, filed on May 18, 2022, and claims priority to German Application No. 10 2021 205 048.4, filed on May 18, 2021. The contents of International Application No. PCT/EP2022/063392 and German Application No. 10 2021 205 048.4 are incorporated by reference herein in their entireties.

FIELD

The invention relates to a knee-joint endoprosthesis comprising a tibia component, which is configured for proximal fixation to a tibia and which has a form-fitting section arranged on an upper face, and comprising a meniscus component, which is configured to articulate with a femoral joint component and which has a complementary form-fitting section arranged on a lower face, wherein the tibia component and the meniscus component are joined together by means of a form-fitting connection formed between the form-fitting section and the complementary form-fitting section.

BACKGROUND

Knee-joint endoprostheses are well known in the field of orthopedic surgery and are intended for use as knee-joint replacements. For example, a knee-joint endoprosthesis with a tibia component and a meniscus component is known from DE 20 2008 004 709 U1. The tibia component is configured for proximal fixation to a tibia. The meniscus component has two bearing shells on its upper face for receiving and supporting femoral condyle surfaces. A lower face of the meniscus component has a meniscus bearing surface which bears slidably on a tibial bearing surface on the upper face of the tibia component.

In addition, the applicant is aware of knee-joint endoprostheses in which the tibia component has a form-fitting section arranged on the upper face and the meniscus component has a complementary form-fitting section arranged on the lower face. In these knee-joint endoprostheses, in contrast to the displaceable bearing between meniscus component and tibia component known from DE 20 2008 004 709 U1, a form-fitting connection is provided between these two components. The meniscus component is immovably fixed on and relative to the tibia component by means of said form-fitting connection, which can be designed, for example, as a plug-in, latching or snap-fit connection.

SUMMARY

The object of the present invention is to make available a knee-joint endoprosthesis of the type mentioned at the beginning that ensures a reliable form-fitting fixation of the meniscus component to the tibia component, while at the same time enabling or at least maintaining compact dimensions and/or conventional material pairings.

This object is achieved by providing at least one reinforcement element which is inserted into the meniscus component, wherein the at least one reinforcement element is configured to mechanically reinforce the form-fitting connection and is arranged in the region of the complementary form-fitting section. The solution according to the invention achieves an effective mechanical reinforcement of the form-fitting connection by simple structural means. According to the invention, no dimensional and/or material-related changes to the form-fitting section and/or the complementary form-fitting section are required. In other words, neither the form-fitting section nor the complementary form-fitting section need be made larger for the purpose of mechanical reinforcement and/or need to be made from materials that can withstand higher mechanical stresses. Instead, the at least one reinforcement element inserted into the meniscus component is provided for the mechanical reinforcement of the form-fitting connection between the tibia component and meniscus component. In this way, the usual dimensions and/or usual materials can be retained both for the tibia component and for the meniscus component, and yet a mechanical reinforcement of the form-fitting connection can still be achieved. The form-fitting connection is preferably non-releasable. That is to say, after the complementary form-fitting section has been joined to the form-fitting section, or the meniscus component to the tibia component, they can preferably not be released non-destructively or can only be released using tools intended for this purpose. The form-fitting connection can be designed in particular as a plug-in connection, latching connection and/or or snap-fit connection Accordingly, the tibia component and the meniscus component, or their respective form-fitting sections, can be plugged together, latched onto each other and/or "snapped" onto each other. The terms "latching connection" and "snap-fit connection" are to be understood as synonymous in the context of this description. The form-fitting connection is preferably designed as a snap-fit connection and/or has at least one snap-fit connection, preferably a plurality of snap-fit connections. The form-fitting connection preferably acts in the proximal-distal direction. Alternatively or additionally, the form-fitting connection preferably acts in the medial-lateral direction. Also alternatively or additionally, the form-fitting connection preferably acts in the ventral-dorsal direction. The at least one reinforcement element mechanically reinforces the form-fitting connection. In other words, the at least one reinforcement element brings about an increased mechanical load-bearing, stress-bearing and/or load-carrying capacity of the form-fitting joint connection. The at least one reinforcement element is manufactured separately from the meniscus component and is then inserted into the latter. "Inserted into the meniscus component" means that the at least one reinforcement element is inserted in particular into a recess, cavity, bore or the like provided for this purpose in the meniscus component and/or is molded into the meniscus component. More preferably, a plurality of reinforcement elements are present and are inserted into the meniscus component at different points in the region of the complementary form-fitting section.

In one embodiment, the tibia component is made of, a preferably metallic, first material at least in the region of the form-fitting section, the meniscus component, at least in the region of the complementary form-fitting section, is made of a, preferably polymeric, second material, which is comparatively less mechanically stressable than the first material, and the at least one reinforcement element is made of a, preferably metallic, third material, which is comparatively more mechanically stressable than the first material and/or the second material. The tibia component is preferably made at least predominantly, preferably completely, from the first material. The meniscus component is preferably made at least predominantly, preferably completely, from the second material. The first material can withstand higher mechanical stresses than the second material. This is the case, for example, when the first material of the tibia component is a metallic material, and the second material of the meniscus component is a polymeric plastic material. The first material is preferably a titanium alloy. The second material is preferably polyethylene. The third material is preferably a titanium alloy. With this embodiment of the invention, a standard material pairing or selection can be retained for the tibia component and meniscus component. In this way, the usual material costs for the tibia component and meniscus component can be maintained despite a reinforcement of the form-fitting joint connection.

In one embodiment, the at least one reinforcement element is made from a X-ray opaque material. Since the at least one reinforcement element is arranged in the region of the complementary form-fitting section, this embodiment of the invention permits simple and reliable X-ray monitoring of the form-fitting connection. That is to say, following the knee-joint replacement operation, a standard X-ray examination can be used to check whether the at least one reinforcement element, and with it the meniscus component, is still at the intended position. X-ray opaque materials are in principle known as such in the field of medical technology. The meniscus component is preferably made from a material that is comparatively less X-ray opaque than the material of the at least one reinforcement element.

In one embodiment, the form-fitting section has a receiving pocket which is sunk into an upper face of the tibia component and which is bordered in the circumferential direction at least in sections by a boundary wall, and the complementary form-fitting section has a receiving foot forming the lower face of the meniscus component, the boundary wall having an inner contour, the receiving foot having an outer contour complementary to the inner contour, and the form-fitting connection having a plurality of snap-fit connections formed between the inner and outer contours. This embodiment of the invention enables the meniscus component to be fixed to the tibia component in a simple yet reliable manner. For this purpose, the plurality of snap-fit connections is formed between the inner and outer contours. Put simply, the meniscus component is latched or “snapped” onto the tibia component. The receiving pocket of the tibia component is open at the top in the proximal direction and is designed to receive the receiving foot of the meniscus component. In other words, the receiving pocket is sunk in the distal direction into the upper face of the tibia component, with the boundary wall forming an edge round the receiving pocket, preferably completely, in the circumferential direction. The receiving foot of the meniscus component forms the lower face of the latter oriented in the distal direction. In an interconnected state, the boundary wall limits a relative mobility of the receiving foot and thus of the meniscus component in the ventral-dorsal and/or medial-lateral direction. The receiving pocket, closed at the bottom in the distal direction, limits the relative mobility in the distal direction. The plurality of snap-fit connections limits the relative mobility in the proximal direction. In other words, the plurality of snap-fit connections prevents the meniscus component from being able to be lifted upward (in the proximal direction) from the tibia component. When the plurality of snap-fit connections is established, the inner and/or outer contour are/is elastically deformed at least in sections, with the actual positive locking being achieved after elastic spring-back. The elastic deformation and spring-back is preferably effected at least predominantly on the part of the meniscus component.

In one embodiment, the at least one reinforcement element mechanically reinforces at least one of the plurality of snap-fit connections. For this purpose, the reinforcement element itself can have a snap-fit geometry configured to interact with the inner contour. Alternatively or additionally, the reinforcement element can reinforce a snap-fit geometry of the outer contour provided for this purpose, for example by being arranged below the outer contour in the thickness direction of the latter. In one embodiment, the at least one reinforcement element reinforces and/or forms a snap-fit edge of the meniscus component.

In one embodiment, the inner contour has a plurality of recesses, the outer contour has a plurality of projections, and in each case one of the plurality of projections interacts with one of the plurality of recesses to form one of the plurality of snap-fit connections, the at least one reinforcement element mechanically reinforcing and/or forming one of the plurality of projections. This is a particularly preferred embodiment of the invention. In an assembled state, the plurality of projections each engage in a respective one of the plurality of recesses. The plurality of recesses each extend into the boundary wall in the direction of thickness of the latter. The recesses can each also be referred to as an indentation, clearance or the like. The plurality of projections each protrude outward from the receiving foot in the normal direction of the outer contour. The plurality of projections can each also be referred to as an elevation, bulge or the like. The at least one reinforcement element forms and/or reinforces at least one of the plurality of projections.

In one embodiment of, the plurality of recesses comprise ventrally arranged first recesses and dorsally arranged second recesses, the plurality of projections comprise ventrally arranged first projections and dorsally arranged second projections, the first projections and the first recesses each forming one of the plurality of snap-fit connections, and the second projections and the second recesses each forming an abutment assigned to the snap-fit connections. Preferably, there are two first recesses, two second recesses, two first projections and two second projections. These are preferably each spaced apart from one another in the medial-lateral direction. The first recesses and first projections are arranged on a front face of the receiving pocket and of the receiving foot, respectively. By contrast, the second recesses and second projections are arranged on an opposite rear face of the receiving pocket and of the receiving foot, respectively. In each case one of the first projections and one of the first recesses interact in a form-fitting manner to form one of the plurality of snap-fit connections. To form the relevant snap-fit connection, the corresponding first projection and/or first recess is elastically deformed, with the form fit being established after the corresponding first projection and/or first recess elastically springs back. The second projections and second recesses each interact to form an abutment. This means that when the snap-fit connections are formed, there is preferably no elastic deformation and/or spring-back in the region of the second projections and second recesses. This embodiment of the invention allows the meniscus component to be fixed manually to the tibia component in a manner that is easy and ergonomically advantageous for an operating surgeon.

In one embodiment, the at least one reinforcement element is a cylindrical reinforcement pin which is inserted into, a preferably ventral-dorsal extending, receiving bore of the meniscus component. This embodiment of the invention permits a particularly simple and therefore comparatively inexpensive construction. The reinforcement pin can be inserted into the receiving bore in a form-fitting, force-fitting and/or cohesively bonded manner. The reinforcement pin is preferably pressed into the receiving bore. For this purpose, an outer diameter of the reinforcement pin is preferably slightly greater than an inner diameter of the receiving bore. The reinforcement pin can be sunk completely into the receiving bore, so that the reinforcement pin does not protrude from the receiving bore. Alternatively and preferably, the reinforcement pin protrudes from the receiving bore at the front end. The receiving bore preferably extends longitudinally in the ventral-dorsal direction and is oriented parallel to a transversal plane of a recipient of the knee-joint endoprosthesis.

In one embodiment, the at least one reinforcement pin has a head section protruding axially out of the receiving bore, with a beveled sliding surface arranged at the front end and with a peripheral lateral surface. When the form-fitting connection, in particular a snap-fit connection, is established, the beveled sliding surface interacts in a sliding manner with a section of the tibia component provided for this purpose. After the form-fitting joint connection, in particular a snap-fit connection, has been established, the peripheral lateral surface engages in a form-fitting manner behind a section of the tibia component provided for this purpose, in particular the inner contour.

BRIEF DESCRIPTION OF THE DRAWINGS

Further advantages and features of the invention will become clear from the following description of a preferred exemplary embodiment of the invention that is shown in the drawings.

DETAILED DESCRIPTION

Figure 1:
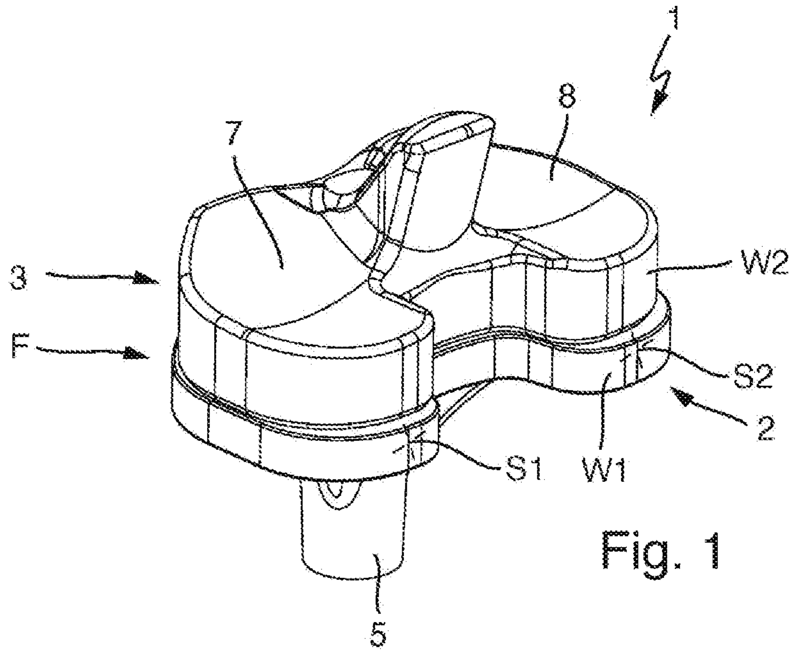
FIG. 1 shows a schematic perspective view of an embodiment of a knee-joint endoprosthesis according to the invention with a tibia component and a meniscus component.
Figure 2:
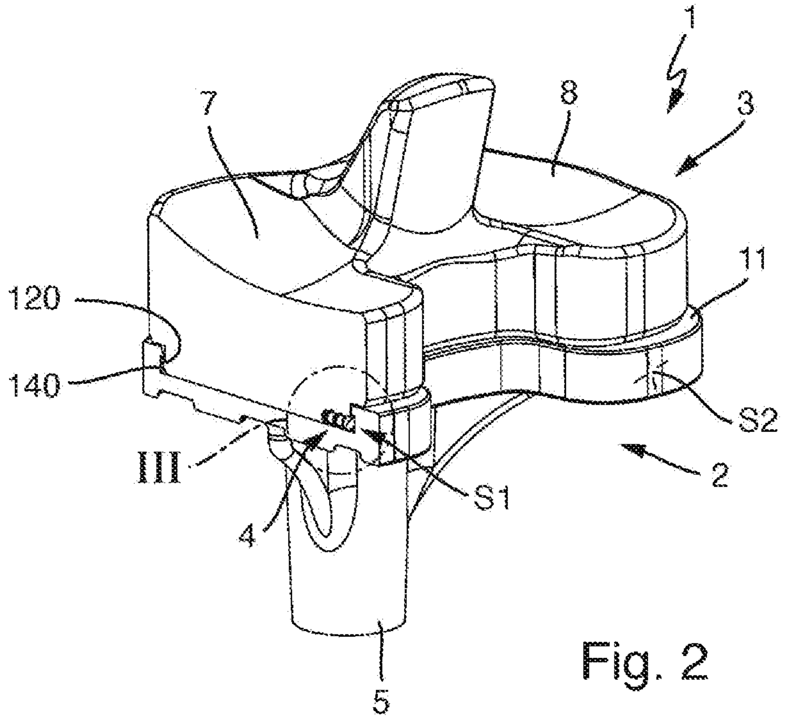
FIG. 2 shows a partially cut-away perspective view of the knee-joint endoprosthesis according to FIG. 1, with a corresponding cutting plane being arranged at the level of a reinforcement element.

According to FIG. 1, a knee-joint endoprosthesis 1 is provided as at least a partial replacement for a human knee joint and has a tibia component 2 and a meniscus component 3. The tibia component 2 and the meniscus component 3 are joined together by means of a form-fitting connection F, which is mechanically reinforced by means of at least one reinforcement element 4 (FIG. 2).

The tibia component 2 (FIGS. 7, 8) is configured for proximal fixation to a tibia. For this purpose, the tibia component 2 in the present case has a shaft section 5 which is arranged on a lower face and which can be implanted in the tibia in a manner known to a person skilled in the art. In order to establish the form-fitting connection F with the meniscus component 3, the tibia component 2 has a form-fitting section 6 on an upper face. The form-fitting section 6 is designed in a manner that will be described in more detail below.

The meniscus component 3 is configured to articulate with a femoral joint component. For this purpose, the meniscus component 3 has an articulation surface 7, 8 arranged on an upper face and intended for sliding articulation with the femoral joint component. The femoral joint component can be a natural or prosthetic joint component. In the embodiment shown, the articulation surface 7, 8 has a medial surface section 7 and a lateral surface section 8, which are spaced apart from each other in the medial-lateral direction. The design and/or function of the upper face of the meniscus component 3 in the region of the articulation surface 7, 8 is known to a person skilled in the art and is not of primary importance as regards the present invention, and therefore further explanations in this connection can be dispensed with. For form-fit interaction with the form-fitting section 6, the meniscus component 3 has a complementary form-fitting section 9 arranged on a lower face. The complementary form-fitting section 9 is designed in a manner that will be described in more detail below, and it can be fixed in a form-fitting manner on the form-fitting section 6 in order to fix the meniscus component 3 to the tibia component 2. In a state when fixed to each other in a form-fitting manner, as is shown in FIG. 1 for example, the form-fitting section 6 and the complementary form-fitting section 9 interact to form said form-fitting connection F.

The at least one reinforcement element 4 is inserted into the meniscus component 3 (FIG. 3) for the mechanical reinforcement of the form-fitting connection F and is arranged in the region of the complementary form-fitting section 9. The at least one reinforcement element 4 brings about an increased load-bearing, stress-bearing and/or load-carrying capacity of the form-fitting connection. This in comparison to an imaginary embodiment without a reinforcement element.

Further structural and functional features of the tibia component 2, the meniscus component 3 and the reinforcement element 4 are explained below. These features are to be considered advantageous in terms of the present invention, but are not necessarily to be considered as essential.

In the embodiment shown, the tibia component 2 is made from a first material W1. The meniscus component 3 is made from a second material W2. The at least one reinforcement element 4 is made from a third material W3.

The first material W1 can withstand higher mechanical stresses than the second material W2. The third material W3 can withstand higher mechanical stresses than the second material W2.

In the present case, a metallic material is selected as the first material W1. A polymeric material, i.e. a plastic material, is selected as the second material W2. The third material W3 is likewise a metallic material.

In the embodiment shown, the first material W1 is a titanium alloy. The same applies to the third material W3. Polyethylene is used as the second material W2.

The reinforcement element 4, more precisely the third material W3, has X-ray opaque properties. In other words, the reinforcement element 4 is at least partially impermeable to X-rays. On account of its X-ray opaque properties, the reinforcement element 4 can be detected comparatively clearly on a corresponding X-ray image. This permits visually simple and reliable monitoring of the relative positioning of the reinforcement element 4 in relation to the tibia component 2 and/or the meniscus component 3. The relative position of the reinforcement element 4 allows conclusions to be drawn regarding how the form-fitting joint connection F ought to be configured to meet the requirements.

Figure 7:
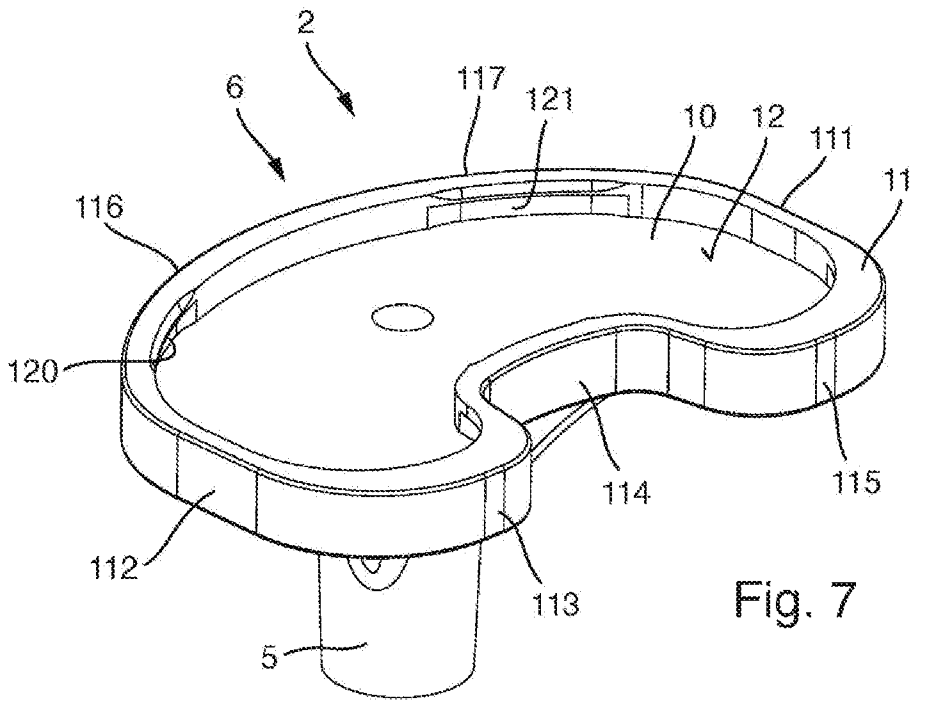
FIG. 7 shows a schematic perspective view of the tibia component of the knee-joint endoprosthesis, looking toward a receiving pocket.
Figure 8:
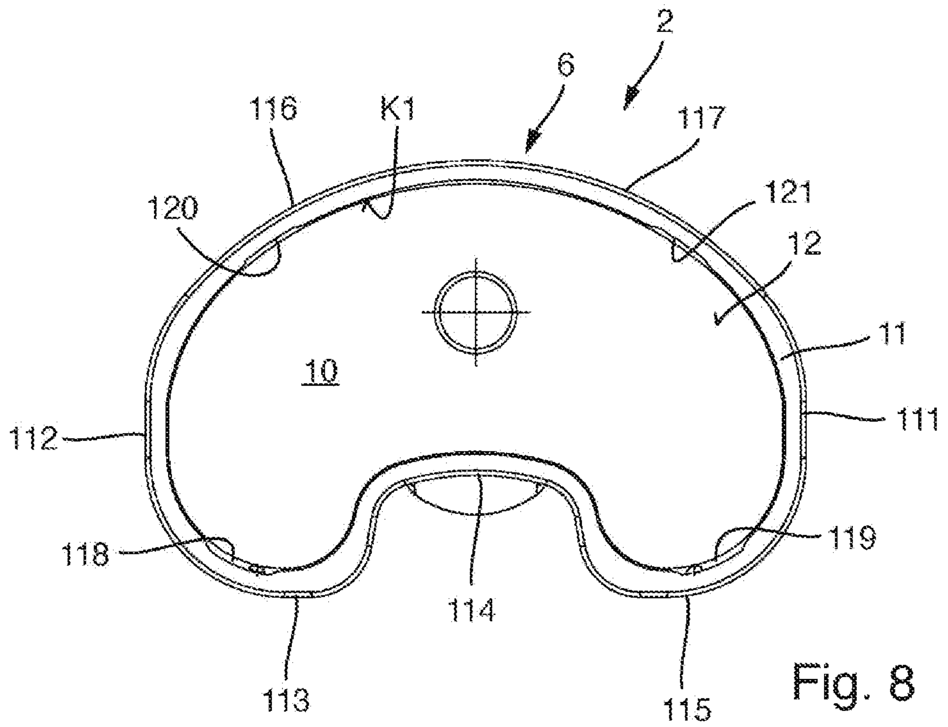
FIG. 8 shows the tibia component in a schematic top view from a distally directed viewing direction.
Figure 9:
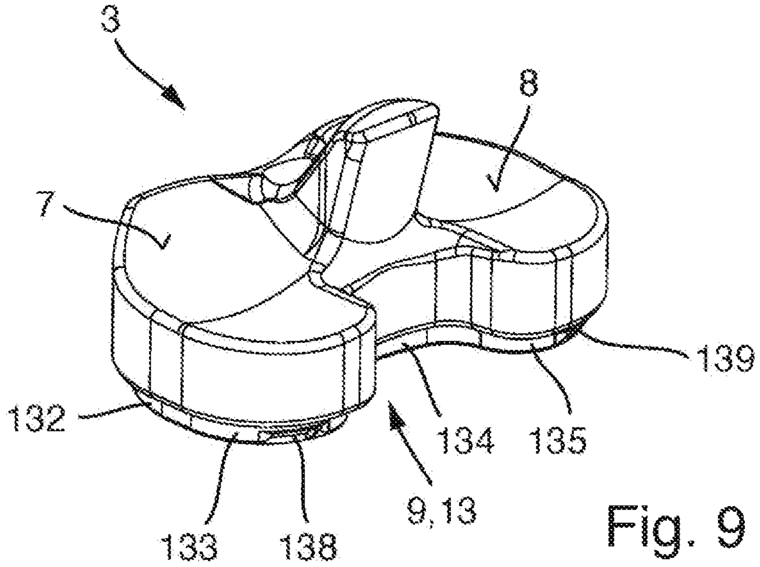
FIG. 9 shows a schematic perspective view of the meniscus component of the knee-joint endoprosthesis.
Figure 10:
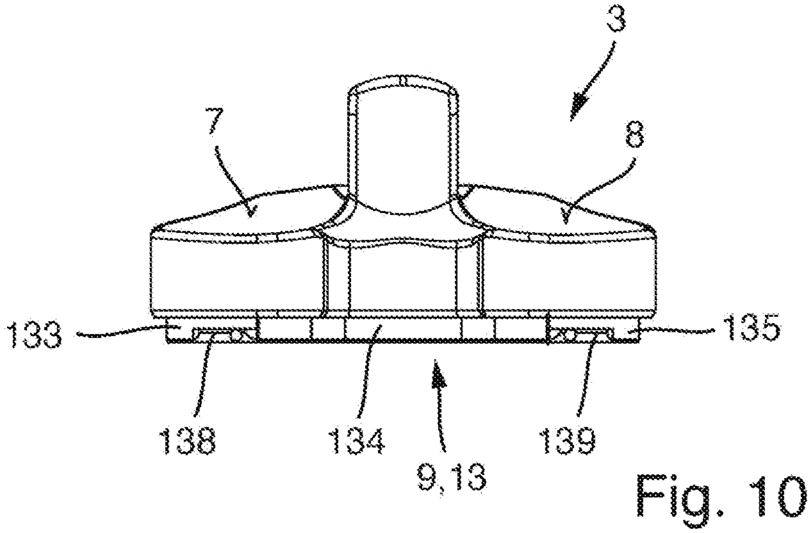
FIG. 10 shows the meniscus component in a schematic front view in a dorsally directed viewing direction.
Figure 11:
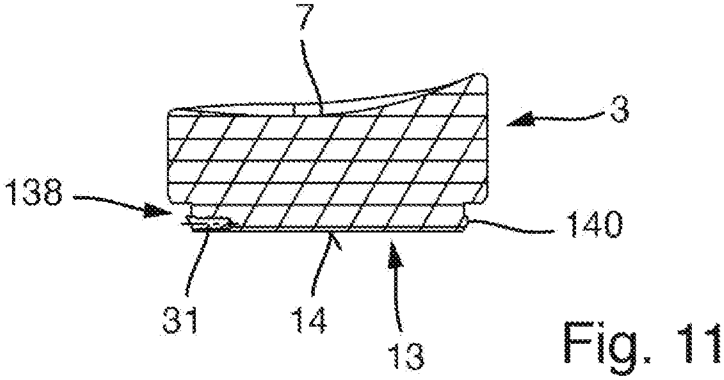
FIG. 11 shows the meniscus component in a sectional view corresponding to FIGS. 5 and 6.

The form-fitting section 6 of the tibia component 2, shown in detail in FIGS. 7 and 8, has a receiving pocket 10 in the embodiment shown. The receiving pocket 10 is sunk into an upper face of the tibia component 2 in the distal direction. In the circumferential direction, the receiving pocket 10 is bordered at least in sections, in the present case completely, by a boundary wall 11. The receiving pocket 10 is open in the proximal direction, i.e. at the top, and is configured to receive the complementary form-fitting section 9. The receiving pocket 10 is delimited in the medial-lateral and in the ventral-dorsal direction by means of the boundary wall 11. The receiving pocket 10 is delimited by a bottom surface 12 in the distal direction. In the embodiment shown, the bottom surface 12 extends flat and, in the state with the knee-joint endoprosthesis 1 implanted in the patient, is oriented parallel to a transverse plane of the patient. The receiving pocket 10 can also be referred to as a receiving recess, receiving depression or the like.

The boundary wall 11 delimits the receiving pocket all the way around. The boundary wall 11 also protrudes from the bottom surface 12 in the proximal direction. The boundary wall 11 has a lateral wall section 111, a medial wall section 112, ventral wall sections 113, 114, 115 and dorsal wall sections 116, 117. In other words, the ventral wall sections 113, 114, 115 are each oriented forward and/or assigned to a front face of the tibia component 2. By contrast, the dorsal wall sections 116, 117 are oriented rearward and/or assigned to a rear face of the tibia component 2. The lateral wall section 111 is oriented outward with respect to a sagittal plane of the patient and/or is assigned to an outer face of the tibia component 2. By contrast, the medial wall section 112 is oriented inward and/or is assigned to an inner face of the tibia component 2.

The boundary wall 11 has an inner contour K1, which is configured to interact with the complementary form-fitting section 9 in a manner that will be described in more detail below. The inner contour K1 extends along a respective inner face of the wall sections 111 to 117. In other words, the inner contour K1 is formed by the inner faces of the wall sections 111 to 117 facing toward the receiving pocket 10. The basic design and/or basic shape of the inner contour K1 and thus also of the receiving pocket 10, as can be seen in particular in FIG. 8, is not necessarily essential in terms of the present invention. Rather, the basic shape corresponds to a customary design known from the prior art. Further explanations in this regard concerning the basic shape of the inner contour K1 and/or of the receiving pocket 10 are not needed in this respect.

Figure 12:
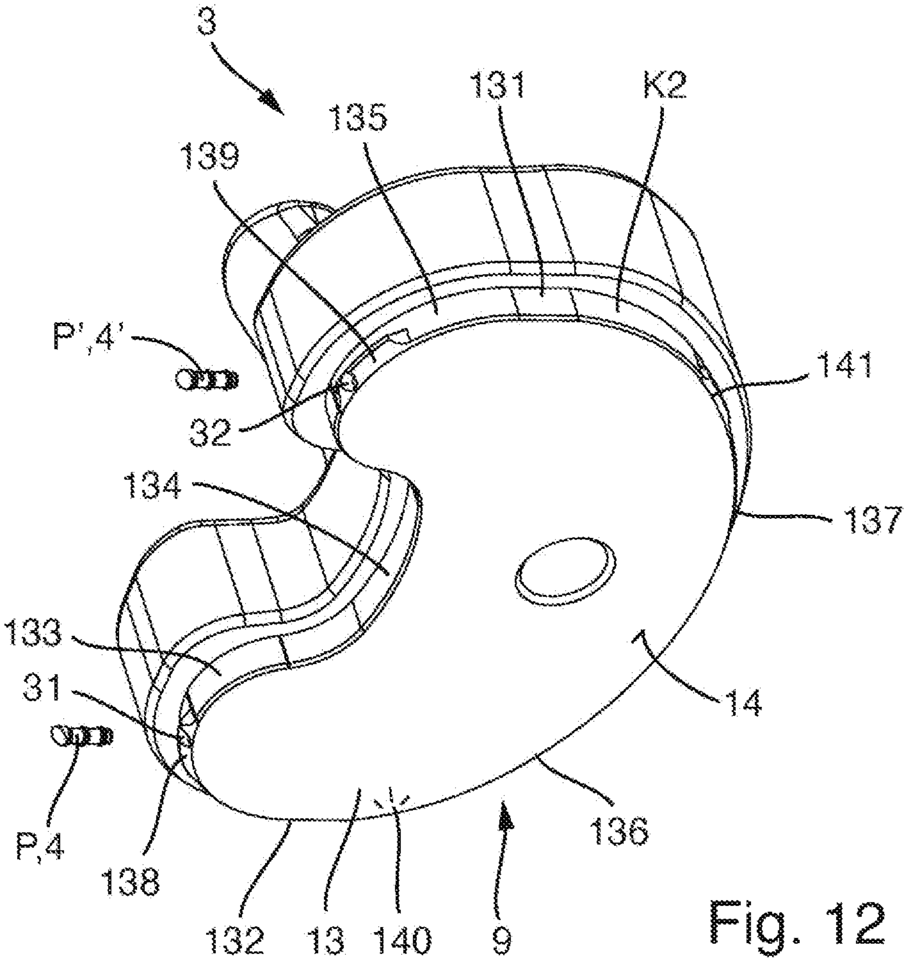
FIG. 12 shows a further schematic perspective view of the meniscus component looking toward an lower face, and together with the reinforcement element and a further reinforcement element.

The complementary form-fitting section 9 of the meniscus component 3 can be seen in detail in particular in FIG. 12 and has a receiving foot 13 forming the lower face of the meniscus component 3. The receiving foot 13 is configured to be received in the receiving pocket 10 and has an outer contour K2, which is designed to complement the inner contour K1. The receiving foot 13 has a distally oriented foot surface 14. In the present case, the foot surface 14 is flat and, in the state implanted in the patient, oriented parallel to the transverse plane. Corresponding to the boundary wall 11 or the inner contour K1 thereof, the receiving foot 13 has a lateral surface section 131, a medial surface section 132, ventral surface sections 133, 134, 135 and dorsal surface sections 136, 137. The surface normals of the surface sections 131 to 137 are each oriented orthogonally to the foot surface 14. Corresponding to the wall sections 111 to 117 of the boundary wall 11, the following applies as regards the orientation and/or assignment of the side surfaces 131 to 137: The lateral surface section 131 is oriented outward with respect to a sagittal plane and/or is assigned to an outer face of the meniscus component 3. By contrast, the medial surface section 131 is oriented inward with respect to the sagittal plane and/or is assigned to an inner face of the meniscus component 3. The ventral surface sections 133, 134, 135 are oriented in the ventral direction and/or are assigned to a front face of the meniscus component 3. By contrast, the dorsal surface sections 136, 137 are oriented in the dorsal direction and/or are assigned to a rear face of the meniscus component 3.

Put simply, the receiving pocket 10 forms a negative impression of the receiving foot 13.

The form-fitting connection F (FIG. 2) is formed between the boundary wall 11 and/or its inner contour K1 and the receiving foot 13 and/or its outer contour K2.

Figure 5:
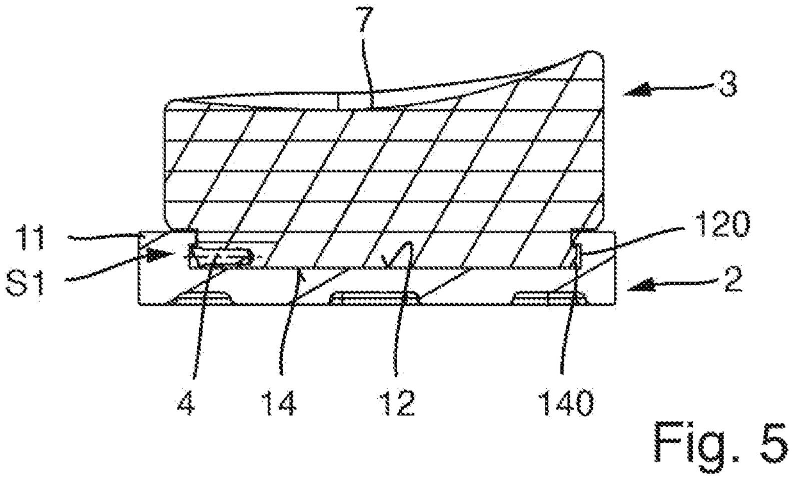
FIG. 5 shows a schematic sectional view of the knee-joint endoprosthesis according to FIGS. 1 to 3 along a sagittal plane and in a medial viewing direction on the least one reinforcement element.

The boundary wall 11 as such limits the relative mobility of the meniscus component 3 in the present case in the medial-lateral direction and ventral-dorsal direction. The relative mobility in the distal direction is limited by the bottom surface 12. The form-fitting connection F is provided to limit the relative mobility in the proximal direction. In the embodiment shown, it has a plurality of snap-fit connections S1, S2 formed between the inner contour K1 and the outer contour K2 (FIGS. 1, 2 and 5). The snap-fit connections S1, S2 are non-releasable in the embodiment shown. This means that after the meniscus component 3 has been fixed once to the tibia component 2, the snap-fit connections S1, S2 can only be released by destroying them and/or using a tool provided for this purpose. In an embodiment not shown in the drawing, the snap-fit connections S1, S2 can instead be designed to be releasable.

The snap-fit connections S1, S2 can also be referred to as first snap-fit connection S1 and second snap-fit connection S2. Both snap-fit connections S1, S2 are arranged on the front face of the knee-joint endoprosthesis 1. In an embodiment not shown in the drawing, the snap-fit connections can instead be arranged on a rear face. An arrangement on opposite outer and inner faces is also conceivable. The present number of two snap-fit connections is also to be understood as purely exemplary. Of course, there can be more than the present two snap-fit connections or just one snap-fit connection.

The at least one reinforcement element 4 serves to reinforce the snap-fit connections S1, S2 in a manner that will be described in greater detail, with a further reinforcement element 4' being present here in addition to the already mentioned reinforcement element 4. The reinforcement elements 4, 4' can also be referred to as first reinforcement element 4 and second reinforcement element 4'. The first reinforcement element 4 is assigned to the first snap-fit connection S1. The second reinforcement element 4' is assigned to the second snap-fit connection S2.

To form the snap-fit connections S1, S2, the inner contour K1 has a plurality of recesses 118, 119, 120, 121 and the outer contour K2 has a plurality of projections 138, 139, 140, 141. The recesses 118 to 121 each extend into the boundary wall 11 in the direction of thickness and can each also be referred to as a depression, indentation or the like. The projections 138 to 141 each protrude laterally from the receiving foot 13. The projections 138 to 141 each extend approximately orthogonally to the normal direction of the foot surface 14. The projections 138 to 141 can each also be referred to as a bulge, protuberance or the like.

The projection 138 and the recess 118 interact to form the first snap-fit connection S1. The projection 139 and the recess 119 interact to form the second snap-fit connection S2. Otherwise, the projection 140 and the recess 120 on the one hand and the projection 141 and the recess 121 on the other hand each interact in a form-fitting manner. Whether, strictly speaking, a snap-fit connection is established by the interaction of the projections 140, 141 with the recesses 120, 121 depends, as will be described in more detail, on the procedure followed by the surgeon when fixing the meniscus component 3 to the tibia component 2. This will be explained in more detail below.

The following also applies as regards the orientation and/or assignment of the recesses 118 to 121 in the embodiment shown: The recess 118 extends in the direction of thickness of the laterally arranged, ventrally aligned wall section 113. The recess 119 is assigned to the wall section 115 in a corresponding manner. The recess 120 is assigned to the wall section 116. The recess 121 is assigned to the wall section 117. In this respect, the recesses 118, 119 can each also be referred to as ventrally arranged recesses. The recesses 120, 121 can also be referred to in the present case as dorsally arranged recesses.

The following applies as regards the orientation and/or assignment of the projections 138 to 141 in the embodiment shown: The projection 138 is arranged on the ventral surface section 133 and projects approximately in the normal direction thereof. Correspondingly, the projection 139 is assigned to the surface section 135. The projection 140 is assigned to the surface section 136. The projection 141 is assigned to the surface section 137. In this respect, it is also possible to refer to ventrally arranged projections 138, 139 and dorsally arranged projections 140, 141.

In the embodiment shown, the reinforcement elements 4, 4' are each assigned to the ventral projections 138, 139. In this case, the projection 138 is reinforced by the first reinforcement element 4. The projection 139 is reinforced by the second reinforcement element 4'.

Figure 4:
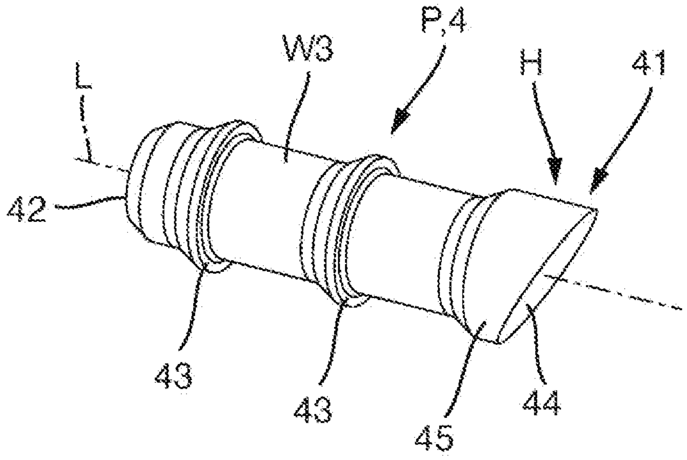
FIG. 4 shows a schematic perspective view of the reinforcement element.

The design of the first reinforcement element 4 is shown in detail in FIG. 4. In the present case, the first reinforcement element 4 is a cylindrical reinforcement pin P, which is axially elongate along a longitudinal axis L between a first front end 41 and a second front end 42. In the present case, the reinforcement pin P has a plurality of radial collars 43 which are spaced apart from one another in the axial direction and beveled on the one side, and which are to be regarded as advantageous but not absolutely necessary. In the region of the first front end 41, the reinforcement pin P has a head section H with a beveled sliding surface 44 and a peripheral lateral surface 45. Moreover, the second reinforcement element 4' is designed identically to the first reinforcement element 4, so that the terms a first reinforcement pin P and a second reinforcement pin P' are also used below.

For mechanical reinforcement of the two snap-fit connections S1, S2, the reinforcement pins P, P' are each inserted in a receiving bore 31, 32 of the meniscus component 3. The receiving bores 31, 32 are each arranged in the region of the complementary form-fitting section 6, more precisely in the region of the receiving foot 13. Specifically, the receiving bore 31 is in the region of the projection 138, and the receiving bore 32 is introduced into the receiving foot 13 in the region of the projection 139. Both receiving bores 31, 32 each extend longitudinally in the ventral-dorsal direction and are oriented parallel to the foot surface 14.

Figure 3:
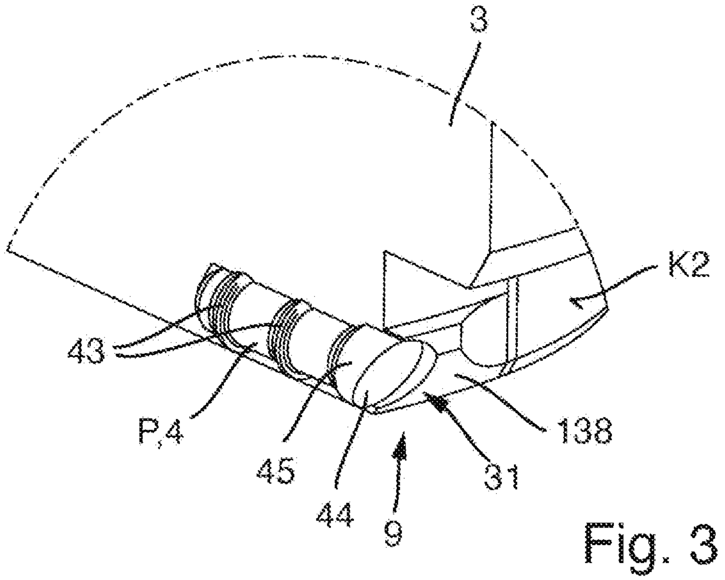
FIG. 3 shows an enlarged detail view of the meniscus component, provided with the at least one reinforcement element, in a region III according to FIG. 2.

FIG. 3 shows that the first reinforcement pin 4 forms a reinforcement of the projection 138 when inserted into the receiving bore 31, to put it simply. The same applies analogously to the second reinforcement pin P' and the projection 139. The reinforcement pins P, P' are pressed into the respective receiving bore 31, 32. The radial collars 43 counteract an unwanted axial displacement of the respective reinforcement pin P, P'. The head section H is arranged directly in the region of the projection 38.

In an embodiment not shown in the drawing, the head section H can form the projection 138.

Figure 6:
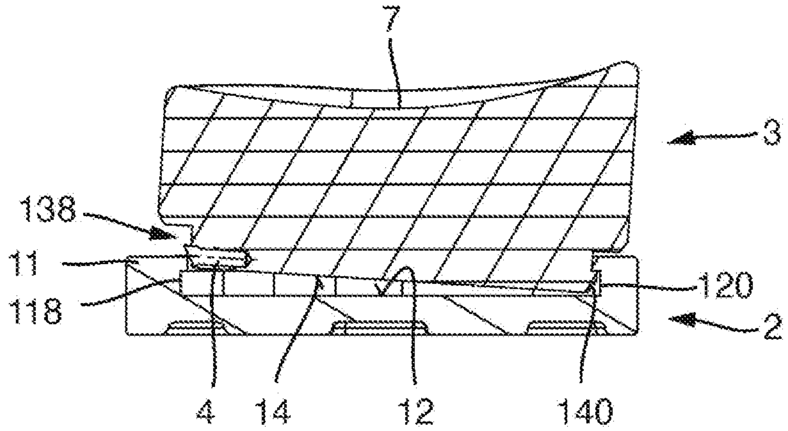
FIG. 6 shows the knee-joint endoprosthesis in a sectional view corresponding to FIG. 5 and in an assembled state in which the meniscus component has not yet been fully assembled with the tibia component.

Fixing the meniscus component 3 to the tibia component 2 can include the steps described below:

The operating surgeon manually grips the meniscus component 3 separate from the tibia component 2 and aligns its receiving foot 13 in the direction of the receiving pocket 10. It will be understood that the tibia component 2 has previously been attached to the tibia in the usual way. The receiving foot 13 is inserted into the receiving pocket 10 in the distal direction, i.e. from the top downward, the meniscus component 3 being aligned slightly obliquely relative to the tibia component 2 (FIG. 6). Here, the dorsal projections 140, 141 are first brought into engagement with the dorsal recesses 120, 121 in a form-fitting manner. Starting from the configuration shown in FIG. 6, the surgeon presses the meniscus component 3 downward. When doing this, the sliding surfaces 44 of the reinforcement pins P, P' interact in a slidable manner with upper edges (not shown in any detail) of the boundary wall 11 in the region of the ventral recesses 118, 119. After latching over or "snapping over" the boundary wall 11, the projections 138, 139 together with the respective reinforcement pin P, P' engage in the respective recess 118, 119. The latching over causes an elastic deformation and subsequent spring-back between the projections 138, 139 and the recesses 118, 119. After the snap-fit connections S1, S2 have been formed, the respective lateral surface 45 of the reinforcement pins P, P' engages behind the respective recess 118, 119 (FIG. 5). The lateral surface 45 can interact directly with the inner contour K1 of the boundary wall 11 or can instead support a section of the outer contour K2 of the receiving foot 13 that interacts with the inner contour K1. In both cases, a mechanical reinforcement of the respective snap-fit connection S1, S2 is achieved.

It will also be seen from FIG. 6 that the dorsal recesses 120, 121 interact with the dorsal projections 140, 141, in each case forming an abutment (not shown in any detail). In other words, it is not absolutely necessary for the projections 140, 141 to latch over the boundary wall 11 in order to be brought into engagement with the respective recess 120, 121.

Of course, a "reverse" fixation of the meniscus component 3 is also conceivable, in which the ventral projections and recesses 138, 139, 118, 119 are first brought into engagement with one another, and then the dorsal projections 140, 141 are brought into engagement with the respective dorsal recess 120, 121 by latching over the boundary wall 11 and in each case forming a snap-fit connection.

The invention claimed is:

1. A knee-joint endoprosthesis comprising:

a tibia component, which is configured for proximal fixation to a tibia and which has a form-fitting section arranged on an upper face;

a meniscus component, which is configured to articulate with a femoral joint component and which has a complementary form-fitting section arranged on a lower face; and at least one reinforcement element, the tibia component and the meniscus component being joined together by a form-fitting connection formed between the form-fitting section and the complementary form-fitting section, the at least one reinforcement element being inserted into the meniscus component and configured to mechanically reinforce the form-fitting connection, the at least one reinforcement element being arranged in a region of the complementary form-fitting section, and the at least one reinforcement element being a cylindrical reinforcement pin that is inserted into a receiving bore of the meniscus component.

2. The knee-joint endoprosthesis according to claim 1, wherein:

the tibia component is made of a first material at least in a region of the form-fitting section, the meniscus component, at least in a region of the complementary form-fitting section, is made of a second material that is less mechanically stressable than the first material, and the at least one cylindrical reinforcement pin is made of a third material that is more mechanically stressable than the first material and/or the second material.

3. The knee-joint endoprosthesis according to claim 1, wherein the at least one cylindrical reinforcement pin is made from an X-ray opaque material.

4. The knee-joint endoprosthesis according to claim 1, wherein:

the form-fitting section has a receiving pocket that is sunk into an upper face of the tibia component and bordered in a circumferential direction at least in sections by a boundary wall, the complementary form-fitting section has a receiving foot forming the lower face of the meniscus component, the boundary wall has an inner contour, and the receiving foot has an outer contour complementary to the inner contour, and the form-fitting connection has a plurality of snap-fit connections formed between the inner contour and the outer contour.

5. The knee-joint endoprosthesis according to claim 4, wherein the at least one cylindrical reinforcement pin mechanically reinforces at least one of the plurality of snap-fit connections.

6. The knee-joint endoprosthesis according to claim 4, wherein:

the inner contour has a plurality of recesses, the outer contour has a plurality of projections, each of the plurality of projections interacts with one of the plurality of recesses to form one of the plurality of snap-fit connections, and the at least one cylindrical reinforcement pin mechanically reinforces and/or forms one of the plurality of projections.

7. The knee-joint endoprosthesis according to claim 6, wherein:

the plurality of recesses comprise first recesses that are ventrally arranged first recesses and second recesses that are dorsally arranged, the plurality of projections comprise first projections that are ventrally arranged and second projections that are dorsally arranged, and the second projections and the second recesses form an abutment assigned to the snap-fit connections.

8. The knee-joint endoprosthesis according to claim 1, wherein the cylindrical reinforcement pin has a head section protruding axially out of the receiving bore, with a beveled sliding surface arranged at a front end and a peripheral lateral surface.

9. The knee-joint endoprosthesis according to claim 8, wherein a portion of the head section facing away from the upper face of the tibia component comprises a cylindrical shape that joins the beveled sliding surface at an acute angle.

10. The knee-joint endoprosthesis according to claim 8, wherein the beveled sliding surface comprises a planar surface and the head section comprises a cylindrical shape that terminates at the planar surface.

11. The knee-joint endoprosthesis according to claim 1, wherein the reinforcement element is configured to create a non-releasable attachment between the form-fitting section and the complementary form-fitting section.

12. A knee-joint endoprosthesis comprising:

a tibia component, which is configured for proximal fixation to a tibia and which has a form-fitting section arranged on an upper face;

a meniscus component, which is configured to articulate with a femoral joint component and which has a complementary form-fitting section arranged on a lower face; and at least one reinforcement element, the tibia component and the meniscus component being joined together by a form-fitting connection formed between the form-fitting section and the complementary form-fitting section, the at least one reinforcement element being inserted into the meniscus component and configured to mechanically reinforce the form-fitting connection, the at least one reinforcement element being arranged in a region of the complementary form-fitting section, and the at least one reinforcement element being a cylindrical reinforcement pin that is inserted into a receiving bore of the meniscus component, wherein:

the tibia component is made of a first material at least in a region of the form-fitting section, the meniscus component, at least in a region of the complementary form-fitting section, is made of a second material that is less mechanically stressable than the first material, and the at least one cylindrical reinforcement pin is made of a third material that is more mechanically stressable than the first material and/or the second material.

13. A knee-joint endoprosthesis comprising:

a tibia component, which is configured for proximal fixation to a tibia and which has a form-fitting section arranged on an upper face;

a meniscus component, which is configured to articulate with a femoral joint component and which has a complementary form-fitting section arranged on a lower face; and at least one reinforcement element, the tibia component and the meniscus component being joined together by a form-fitting connection formed between the form-fitting section and the complementary form-fitting section, the at least one reinforcement element being inserted into the meniscus component and configured to mechanically reinforce the form-fitting connection, the at least one reinforcement element being arranged in a region of the complementary form-fitting section, and the at least one reinforcement element being a cylindrical reinforcement pin that is inserted into a receiving bore of the meniscus component, wherein:

the form-fitting section has a receiving pocket that is sunk into an upper face of the tibia component and bordered in a circumferential direction at least in sections by a boundary wall, the complementary form-fitting section has a receiving foot forming the lower face of the meniscus component, the boundary wall has an inner contour, and the receiving foot has an outer contour complementary to the inner contour, and the form-fitting connection has a plurality of snap-fit connections formed between the inner contour and the outer contour.

* * * * *